United States Patent [19]
Burgess

[11] Patent Number: 6,007,459
[45] Date of Patent: Dec. 28, 1999

[54] METHOD AND SYSTEM FOR PROVIDING PHYSICAL THERAPY SERVICES

[76] Inventor: Barry Burgess, 118 W. MacDonald Ave., Richmond, Calif. 94801

[21] Appl. No.: 09/059,177

[22] Filed: Apr. 14, 1998

[51] Int. Cl.⁶ ........................................... A61B 5/02
[52] U.S. Cl. ................................................. 482/4; 600/301
[58] Field of Search .......................... 482/1–9, 900–902; 600/483, 300, 301; 128/904; 601/23; 364/400, 410.1

[56] References Cited

U.S. PATENT DOCUMENTS

| | | |
|---|---|---|
| H958 | 8/1991 | DeVita, Jr. et al. . |
| 4,151,407 | 4/1979 | McBride . |
| 4,464,122 | 8/1984 | Fuller et al. . |
| 4,631,580 | 12/1986 | Taube et al. . |
| 4,733,354 | 3/1988 | Potter et al. . |
| 4,764,840 | 8/1988 | Haskin . |
| 4,858,121 | 8/1989 | Barber et al . |
| 4,945,410 | 7/1990 | Walling . |
| 4,969,096 | 11/1990 | Rosen et al. . |
| 5,020,528 | 6/1991 | Myers . |
| 5,253,164 | 10/1993 | Holloway et al. . |
| 5,262,943 | 11/1993 | Thibado et al. . |
| 5,265,010 | 11/1993 | Evans-Pagenelli et al. . |
| 5,299,121 | 3/1994 | Brill et al. . |
| 5,357,427 | 10/1994 | Langen et al. . |
| 5,404,292 | 4/1995 | Hendrickson . |
| 5,441,047 | 8/1995 | David et al. ............................ 600/483 |
| 5,471,382 | 11/1995 | Tallman et al. . |
| 5,473,537 | 12/1995 | Glazer et al. . |
| 5,474,090 | 12/1995 | Begun et al. . |
| 5,517,405 | 5/1996 | McAndrew et al. . |
| 5,553,609 | 9/1996 | Chen et al. . |
| 5,594,638 | 1/1997 | Iliff . |
| 5,596,994 | 1/1997 | Bro . |
| 5,660,176 | 8/1997 | Iliff . |
| 5,706,801 | 1/1998 | Remes et al. . |
| 5,720,770 | 2/1998 | Nappholz et al. . |

OTHER PUBLICATIONS

Hanoun Medi Sport Inc., MCRP Information Package, 1996, USA.
JTECH Medical Industries, RangeTrack, USA.
Telemedicine, A Guide to Assessing Telecommunications in Health Care, http://www.nap.edu/readingroom/book/telemed/summary.html. USA.
United Stated General Accounting Office, Telemedicine, Federal Starategy is Needed to Guide Investments, Februaryt 1997, USA.
Tracker ME Series, Jtech Medical Industires (promotional document 2pp).

*Primary Examiner*—Glenn E. Richman
*Attorney, Agent, or Firm*—Kevin H. Fortin, Esq.

[57] ABSTRACT

A method and system for providing physical therapy to a human client having a physical condition includes the steps of providing an electronic communication link between the client and a therapist, instructing the client to move in a particular manner, or to assume a sustained posture or perform a test. Then, feedback is requested from the client. The feedback relates to bodily sensation corresponding to the movement or sustained posture and can be audio, video, and/or data type feedback. The communication link communicates the feedback to the therapist. Accordingly, the therapist utilizes the feedback to assess the physical condition of the client. The therapist also communicates remedial movements or a remedial sustained posture to the client to address the physical condition. Various postural measurements and testing devices are be used in conjunction with the present invention to facilitate assessment and help address the physical condition in accordance with accepted physical therapy techniques.

21 Claims, 5 Drawing Sheets

METHOD AND SYSTEM FOR PROVIDING PHYSICAL THERAPY SERVICES

BACKGROUND OF THE INVENTION

1. Field of the Invention

The present invention pertains to methods for providing physical therapy, and more particularly to providing physical therapy services via an electronic communication system.

2. Previous Art

During the past few decades the demand for physical therapy services has risen. Therapists have grown in number. Injury victims, including those experiencing pain or immobility, commonly see a physical therapist during medical treatment and expect the therapist to address the pain or immobility.

During a typical physical therapy session, the therapist assesses a client's physical situation by reviewing relevant medical records and by direct observation of the client. Often the therapist's remedial techniques include hands-on treatment. Such treatment may include massage, joint manipulation and postural adjustments. Often the client's response to hands-on treatment is used to enable the therapist to further understand, and remedy the client's condition.

Various techniques of providing physical therapy are taught to and typically used by physical therapists. These techniques are implemented through multiple of named physical therapy systems. One such system is known as the "McKenzie Method"—named after Robin McKenzie who developed specific techniques for treatment of spinal pain and other associated issues in New Zealand beginning in the middle part of this century. Robin McKenzie has published multiple books including *Treat Your Own Back, Treat Your Own Neck, The Lumbar Spine, The Cervical and Thoracic Spine.* The McKenzie Method is now a widely acclaimed and accepted system of treatment.

The McKenzie Method and other therapy systems use mechanical diagnosis and treatment of a client's condition to reduce pain. One unique feature of this type of therapy is that the therapist instructs the client to practice a particular movement or sustained posture to facilitate mechanical diagnosis and treatment. The client provides feedback relating to the movement or sustained posture. For example, the client's feedback may describe attributes of pain experienced during and after each movement or sustained posture. From this feedback, additional movements and postures are instructed for further diagnosis and for treatment. This instruction/feedback methodology repeats and is therapeutic when practiced according to a skilled therapist's instruction.

A limitation of providing physical therapy generally is that the therapist and the patient are located together. This restricts the access of some patients to some therapists and also provides time limitations on how many patients a traveling therapist can visit in a day.

One benefit of the McKenzie method is that hands on manipulation, while useful, is not generally unnecessary to successfully treat a client. On the contrary, this and other types of physical therapy services can be competently provided through iterations of visual observation and verbal instructions relating to remedial postures or therapeutic movement.

Telemedicine is an idea that has drawn recent attention from military, government, medical professionals, insurers and computer/software specialists. Telemedicine is the provision of health care consultation and education using telecommunication networks to communicate information, and practice medicine via telecommunications and interactive video technology. Telemedicine typically involves the real time or near real-time transfer of medical information between places. Some medical systems now rely on telemedicine.

U.S. Pat. No. 5,553,609 to Chen et al., discloses a network employing audio-visual technology to link a patient with a remote care-giver. Data and video are transferred between the caregiver and the patient to enable the patient to have access to a remote, or multiple remote caregivers. The network includes a database with accessible patient information to assist caregivers in diagnosis and treatment. This network relies on bodily condition sensors and other appliances, which may be controllable by the caregiver, to monitor a patient. The video technology, in particular, is remotely controlled to enable the caregiver to visually search particular areas. The audio technology enables the caregiver to listen to sounds made by the patient. There is no disclosure, however, of addressing a physical condition by applying such a system. There is also no disclosure using physical therapy techniques in conjunction with such a system.

While telemedicine is making great strides, there is still an unmet need to provide physical therapy services to all the patients who would benefit from such service. There is also a need to enable a patient to see any of a number of physical therapists without undue burden. Methods of providing physical therapy services are sought which are cost-effective, readily available and which can help the physical condition of a physical therapy client.

SUMMARY OF THE INVENTION

A method for providing physical therapy to a human client having a physical condition includes providing an electronic communication link between the client and a therapist. The communication link provides sound and video images of the patient to the therapist, and vice-versa.

The therapist instructs the client to move in a particular manner, or to assume a sustained posture. The therapist then requests feedback from the client relating to bodily sensations corresponding to the movement or sustained posture and simultaneously observes visual data indicative of qualities of client movement. The communication system communicates the feedback to the therapist via the electronic communication link. Accordingly, the therapist utilizes the feedback to assess the physical condition of the client. The instructions, feedback, and any assessment or response by the therapist to the feedback iteratively repeat. The feedback, for example, may include postural measurement data. Video images enable communications between the therapist and the client to be communicated both verbally and by gesture.

In addition to making an assessment, the therapist may also address the client's physical condition through the interactive communications. Preferably, the therapist communicates instructions for therapeutic movements and/or remedial sustained postures to the client to iteratively address the client's physical condition and to reduce pain. Such instruction is in accordance with the McKenzie Method, or other accepted physical therapy method. The steps leading to assessment and remedy repeat to iteratively address the client's physical condition.

In accordance with the invention, the electronic communication link includes a first terminal associated with the client and a second terminal associated with the therapist.

The client provides audio sound and video images at the first terminal and the therapist provides audio sound and video images at the second terminal. The electronic communication link communicates audio and video data between the first terminal and the second terminal to enable remote diagnosis and treatment of the client's physical condition.

DETAILED DESCRIPTION OF THE INVENTION

Figure 1:
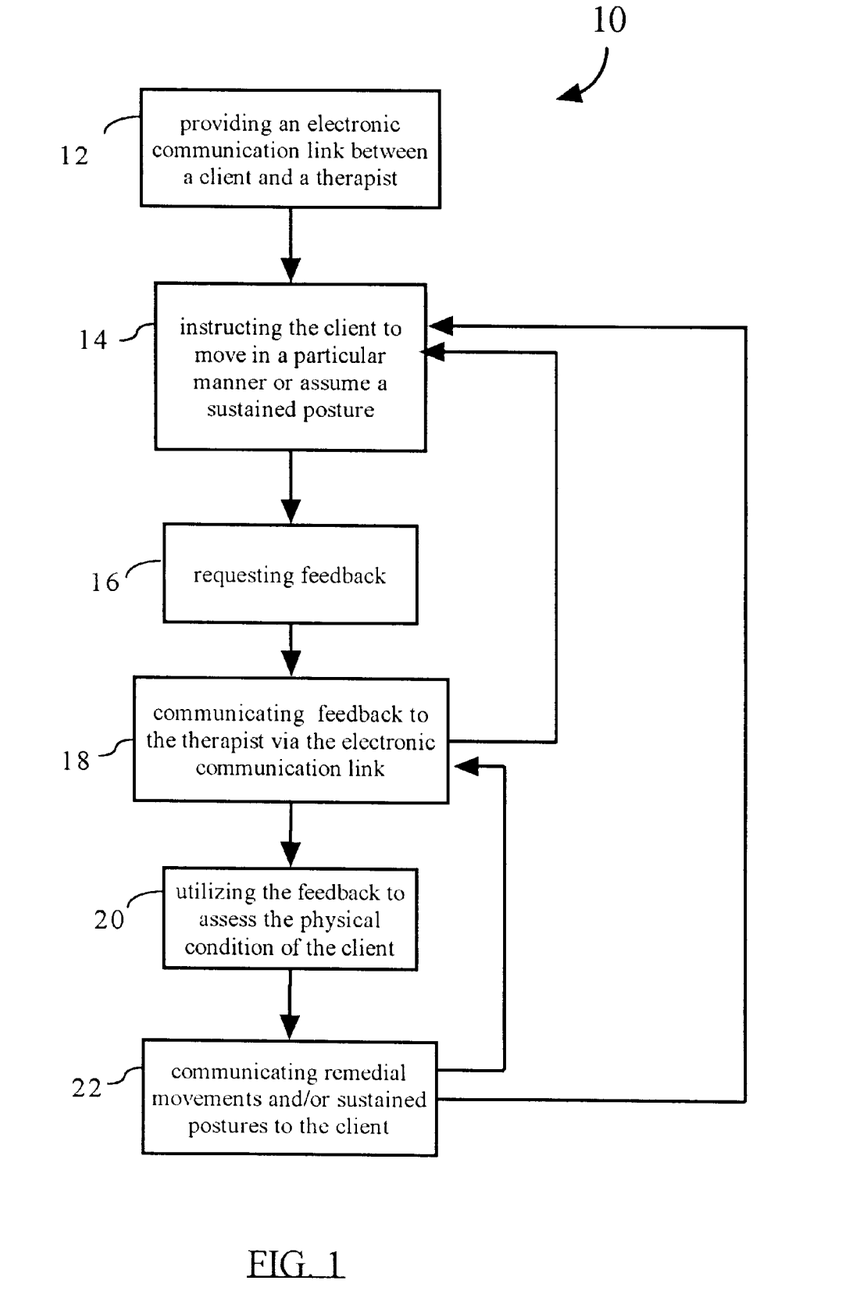
FIG. 1 is a flowchart showing a method in accordance with the present invention.

FIG. 1 shows a method 10 for treating pain, parasthesia, immobility and other physical conditions with physical therapy. The method 10 includes the step 12 of providing an electronic communication link between a human client and a therapist, the step 14 of instructing the client to move in a particular manner, or to assume a sustained posture, the step 16 of requesting feedback from the client relating to bodily sensation corresponding to the movement or sustained posture, the step 18 of receiving the feedback from the client, the step 20 of utilizing the feedback to assess the physical condition of the client, and the step 22 of communicating remedial movements or a remedial sustained posture to the client to address the physical condition.

According to one aspect of the invention, steps 14, 16 and 18 repeat to enable the therapist to iteratively assess the physical condition of the client. The steps 18, 20, and 22 repeat to iteratively address the physical condition of the client. According to another aspect of the invention steps 14, 16, 18, 20 and 22 iteratively repeat to integrate the assessment and therapeutic aspects of the method 10. The method 10 is preferably performed in accordance with the McKenzie method of physical therapy.

The electronic communication link, through communicated audio, video and data, enables iterative assessment and remedial therapy to help a client address a physical condition such as pain, parasthesia, and restricted movement from a remote location.

Applying the McKenzie method in conjunction with the present invention to address neck pain, for example, would involve instructing the client the client to flex and/or rotate at the neck through at least one, and likely numerous iterations. Each iteration is precisely performed and closely scrutinized in accordance with the McKenzie method of mechanical diagnosis and treatment. The video aspect of the present invention is very useful to enable the therapist to gather feedback and to enable implementation of the McKenzie methodology.

To address back problems, the step 14 of instructing the client includes, for example, instructing the client to flex and/or rotate his torso. Instructions are specified by the therapist and communicated to the client via the communication link. The therapist observes resulting movements and other feedback, which may include postural measurement data from the client, and provides additional instructions accordingly. The communication link enables feedback in many forms including sounds, gestures, and words.

The McKenzie method has numerous foundational exercises which, when performed properly, can reduce pain, increase postural awareness, and address many of a number of physical issues which the client may encounter. This invention enables a therapist at a remote location to view the client via the communication link to insure that the communicated exercises and/or sustained postures, such as promoted by the McKenzie method, are properly carried out by the client.

Sustained postures and particular exercises are known to remedy pain and other physical issues under a variety of therapeutic systems. According to a client's needs, the step 22 of communicating remedial movement includes communicating an exercise to the client to reduce pain and address the physical condition which may include poor posture. This communication can be subtle, in the form of a gesture or expressed verbally. The client's responses to exercise is observed by the therapist. During the exercise, the therapist may choose to modify the client's posture and/or technique to achieve optimal results. The therapist can demonstrate selected exercises and sustained postures via the communication link using vocal instruction, gestures or both. It can be appreciated that the present invention can also provide written instructions for the sensory impaired.

Therapists often work with clients who experience movement of pain from one bodily location to another in response to the instructed movement or particular posture. The step 18 of communicating feedback includes the therapist receiving a description of the experience of pain from the client. This description can be verbal, or the client can gesture to show where pain lies, and to describe how the pain is felt during a therapy session. The therapist utilizes the feedback to assess the physical condition of the client. The therapist, through direct observation, may, for example, understand the client's sense of movement of pain from one bodily location to another in response to a particular instructed movement or a particular instructed posture.

According to one embodiment of the inventive method, the step 10 of providing an electronic communication link includes providing the therapist with a client medical history. The step of providing the therapist with a client medical history may be initiated by the therapist and accomplished by electronically accessing a remote data base, or by direct communication with the client. The electronic communication link can communicate with the database either via the Internet, satellite link, or a dial-up link, for example.

Figure 2:
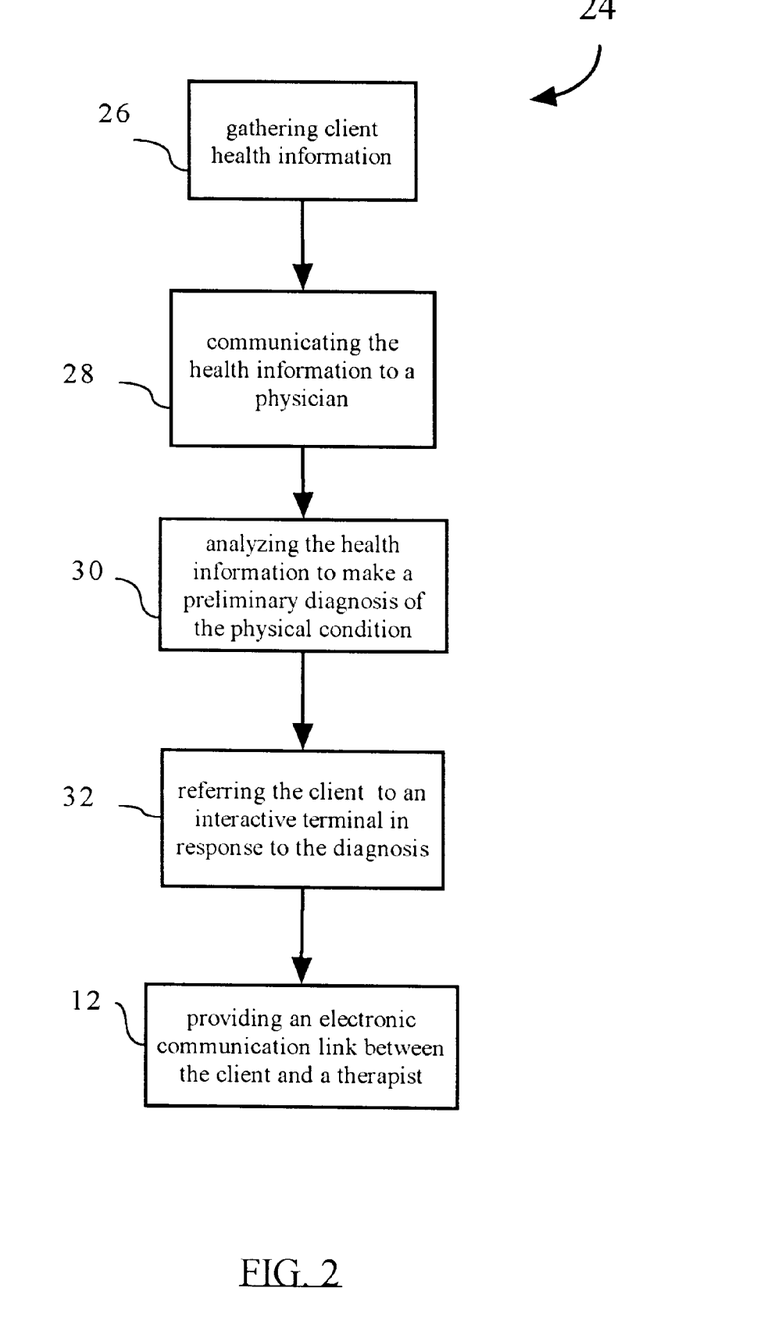
FIG. 2 is a flowchart showing additional steps useful with the method of FIG. 1.

FIG. 2 shows a method 24 including the step 26 of gathering client health information including a complaint of a physical condition, the step 28 of communicating the information to a physician, the step 30 of analyzing the information to make preliminary diagnosis of the physical condition, the step 32 of referring the client to an interactive terminal, and the step 12 of providing an electronic communication link between the client and a therapist.

In response to the preliminary diagnosis, the step 32 refers the client to an interactive terminal, which links the client and remotely located physical therapist through video images and sound. The steps of FIG. 2 enable a therapist, who is not a physician, to communicate with a physician and obtain a preliminary diagnosis in accordance with accepted medical practices.

Figure 3:
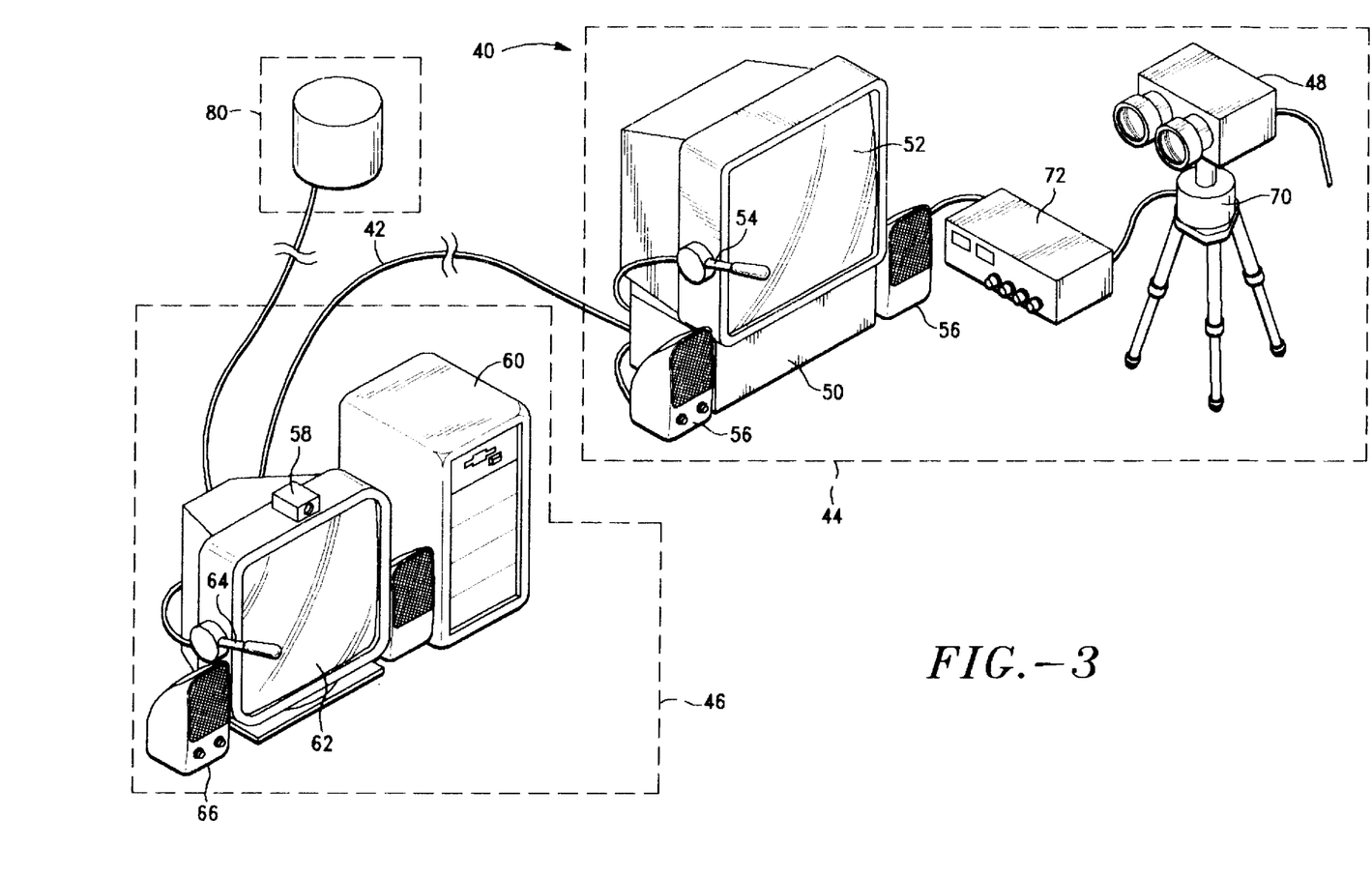
FIG. 3 is a diagram of a system in accordance with the present invention which includes stereoscopic camera.

FIG. 3 shows a system generally designated with the reference numeral 40 in accordance with the present invention. The system 40 includes a communication link 42, a first terminal 44 associated with a client and a second terminal 46 associated with a therapist. The first terminal 44 includes a video camera 48, a computer 50, a display 52, a microphone 54 and speakers 56, which operably interconnect. The second terminal 46 includes a video camera 58, a computer 60, a display 62, a microphone 64 and speakers 66, which operably interconnect. The first terminal 44 and second terminal 46 are capable of computing, multimedia display, video and audio recording, and remote communication. The first terminal 44 communicates directly with a client. The second terminal 46 communicates directly with a therapist.

The video camera 48 of the first terminal 44 is a stereoscopic 3-D camera and includes a remote controllable motor 70 for moving the camera 48 and control unit 72. The video camera 58 of the second terminal 46 is fixed.

The second terminal 46 remotely controls the video camera 48 of the first terminal 44 to enable the therapist to clearly view the client in any of a number of postures and at any of a number of focal distances with respect to the first terminal 44. In particular, the second terminal regulates focus, zoom, rotation and other movement of the first terminal video camera 48. This remote control feature enables the therapist to continually observe the client when the system 40 is in use and to follow movement of the client under circumstances such as where movement is required to assess and remedy the client's condition. Lighting adjustments at the first terminal are remotely controlled by the second terminal. Such adjustments include adjustment to direction, intensity and diffusion. It can be appreciated that this remote control feature can be automated and regulated by the first terminal computer 50, or other device.

The microphone 54 and video camera 48 connect to the computer 50 automatically input audio sound and video images into the first terminal computer 50. These images and data are converted by the controller 72 and cached by the computer 50 for communication to the second terminal 46.

The microphone 64 and video camera 58 of the second terminal 46 automatically input audio and video into the computer 60 at the second terminal 46. This audio and video input is communicated to the first terminal 44 at the same time that the first terminal 44 communicates images and data to the second terminal 46.

The electronic communication link 42 simultaneously communicates audio and video between the first terminal 44 and the second terminal 46. It can be appreciated various ways are known, and which may be developed to enable the electronic communication link 42. These ways include the Internet, an Intranet, and telecommunications, satellite and cable systems communications.

According to one aspect of the invention the second terminal 44, or first terminal 46, is equipped with the appropriate software to enable video images captured by the first terminal camera 48 to be dissected by an appropriate algorithm to measure client postural information, including movement. Information such as range of motion, postural alignment, rate of change of particular movements and other postural information for any particular body part can be precisely determined by dissecting the video images and evaluating the dissected video images. This information, especially the range of motion information, is useable by the therapist in making client records, in assessment and in providing remedial instructions to the client.

Employing the computer 50 to analyze measurements of a client's motion or posture is particularly useful in cases where such information is sought to be shared, along with video images, between any of a number of caregivers including physicians, and other therapists. Sharing the information is useful not only for case conferencing, but also for educating less experienced therapists.

According to one aspect of the invention, the second terminal video camera includes a stereoscopic 3-D video camera. The communication link 42 communicates stereoscopic video images between the first terminal and the second terminal. The second terminal display displays the stereoscopic images to enable the therapist to view the patient in 3-D. Stereoscopic imaging also enables the computer 60 of the second station terminal 46 to accurately analyze the video images, or still images.

The system 40 includes a client information database 80. The database 80 is accessible via the communication link 42 to provide the therapist with a client health history in conjunction with the video, audio and client postural data. According to one aspect of the invention, the database 80 is remotely located. According to another aspect of the invention, the database 80 is part of either the first or second terminal to supplement feed back obtained from the client.

Figure 4:
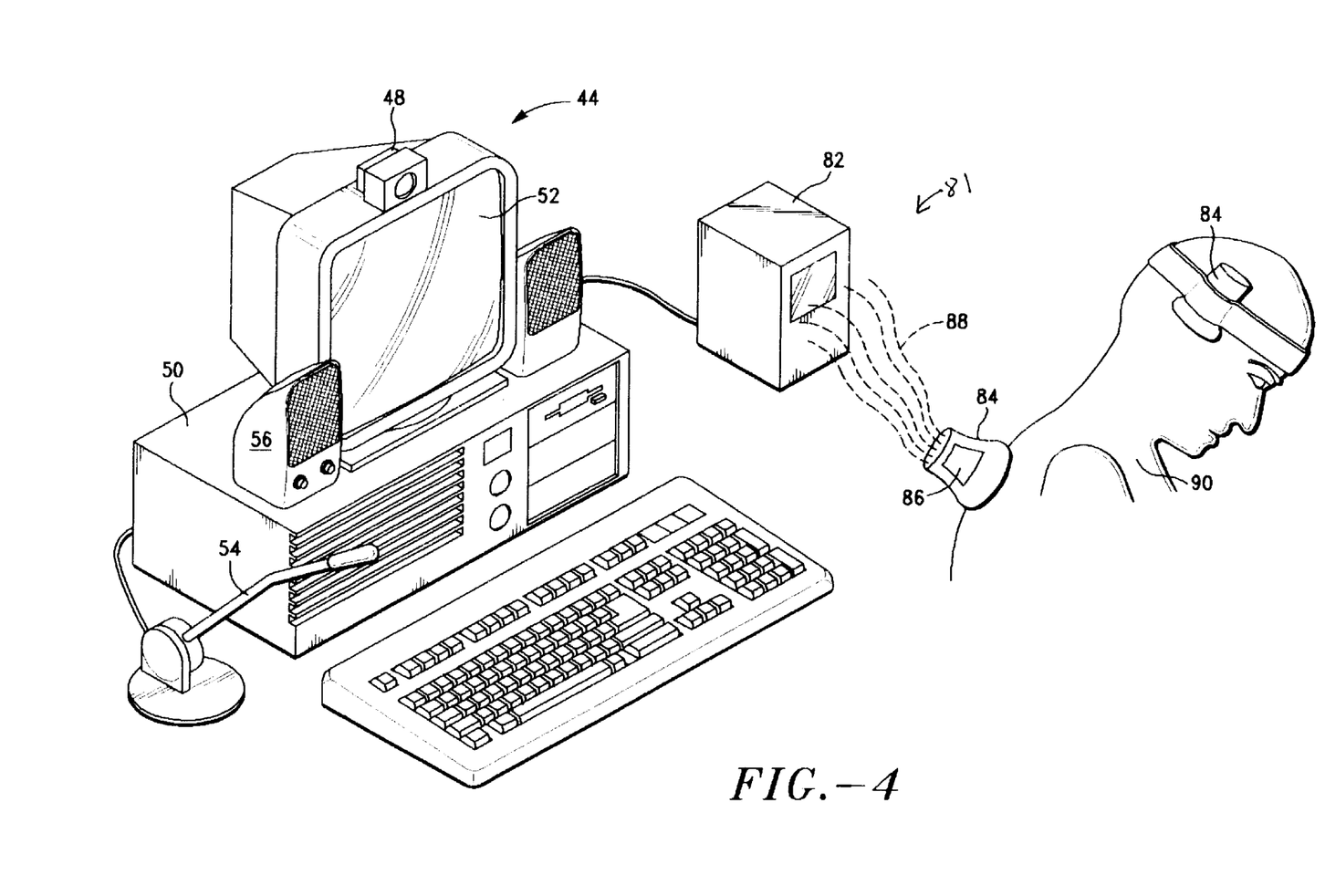
FIG. 4 is a diagram of a system employing an inclinometer and an infrared receiver in accordance with the present invention.

FIG. 4 shows the first terminal 44 coupled with a postural measurement device generally designated with the reference numeral 81. The postural measurement device 81 includes an infrared receiver 82 coupled with the first terminal 44 and a pair of inclinometers 84 attached to a client 90. At least one inclinometer 84 includes an infrared transmitter 86. The infrared receiver 82 couples with the first terminal computer 50 and generates an infrared signal 88 reflective of client postural information. Accordingly, the inclinometers 84 transmit signals relating to client postural information to the first terminal 44 via the infrared receiver 82. The first terminal 44 communicates the signals to the second terminal 46 via the communication link 42. Thus, the therapist immediately accesses client postural information gathered by each inclinometer (see FIG. 3). Inclinometers, in accordance with the present invention are to include all devices which measure postural information, i.e. the angles between various selected bodily parts. Preferably, video, audio, and postural information is simultaneously transmitted to the therapist at the second terminal.

The inclinometers 84 are preferably DUALER PLUS™ inclinometers such as marketed by Jtech Medical Industries. Inclinometers 84 are shown by way of example because inclinometers 84 measure postural information. It can be appreciated that there are a variety of alternate ways to measure postural information, and a number of alternate postural measurement devices, which may be coupled in communication with the first terminal.

A goiniometer, an accelerometer, a dynamometer, reflex testing device or other postural measurement device may couple with the first terminal 44 and attach to the client 90 to measure postural information and communicate the measured postural information to the first terminal 44.

An SEMG system, for example as marketed by Jtech Medical Industries under the name DYNA TRACK, measures postural muscles through dynamic EMG study. Such a system is incorporated into the system and method of the present invention, according to one aspect of the invention.

A MCRP™ (Multi-Cervical Rehabilitation Program) device such as marketed by Hanoun Medi-Sport, Inc. for isometric, dynamic, angle specific, and range of motion assessment and rehabiltation includes a seated exercise and diagnostic station. Such a station couples with the first terminal in accordance with one aspect of the invention. Accordingly, data relating to the client's physical condition can be assessed and addressed from a remote location.

Anesthesiometric devices test nerve response such as sensation in limbs, for example. Such devices are useful in the physical therapy context to determine the efficacy of therapy in the correction of paresthesia.

Data reflective of each postural measurement is communicated via the communication link to the second terminal 46 therapist. Postural information is information pertaining to the body, which affects posture. This includes postural angles at various joints and distances between particular points of the body. Postural information also includes range of motion determinations and rates of change of such determinations so that progress can be plotted. Qualities of movement e.g. and pathways of movements and movement rates are considered postural information. Additionally, information associated with physical and emotional reactions to particular postures or movements is considered postural information. The strength of a particular group of muscles, or an individual muscle, may affect posture, accordingly there are times when muscle strength information is important postural information.

Accelerometers, or similar devices coupled to the patient at various points and in communication with the first terminal, for example, can facilitate measurement of rates of postural changes to quantify aspects of pathways of movement or other components of movement.

The postural measurement device 81 may include a neural conductivity measurement device coupled with the first terminal for measuring client neural conductivity. Such a neural conductivity device includes multiple skin surface electrodes. Some of the electrodes discharge electrical impulses to stimulate a selected region of the client. Other of the electrodes sense the client's response to assess nerve conductivity.

Alternately, the postural measurement device 81 includes a skin surface EMG measurement device to detect changes in skin surface EMG for any of a variety of postures because it is known that posture and movement effect many bodily functions, including electrical responses.

In one variation of the invention, the postural measurement device 81 includes a thermometer to measure changes in body temperature at a selected location, for any of a variety of postures. Temperature variations may sometimes indicate problematic regions of the body. In another variation, the postural measurement device 81 includes a protractor such as an arthrodial protractor to provide a reference grid for video images.

According to one aspect of the invention, the postural measurement device 81 includes a muscle strength-testing device. For example, a resistance meter, which measures hand, or arm, muscle strength, can be used. Alternately, the strength measuring device includes an exercise station with variable resistance which enables muscle exercise in addition to strength testing.

Figure 5A:
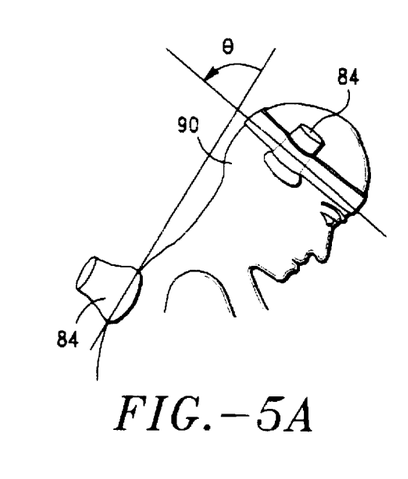
FIGS. 5a, 5b, 5c, 5d, and 5e show a client being connected with an inclinometer.

FIG. 5a shows a client with a pair of inclinometers attached. Combined, the inclinometers measure the maximum range of motion of the neck in the forward bending direction. Additionally, the inclinometers can measure the angle of the neck during postural correction exercises communicated by the therapist. This enables the therapist to use this information to gauge therapeutic success.

The inclinometers 84 misalign at the angle θ. Accordingly, measurements from each inclinometer 84 can be used to calculate the angle θ, which represents the degree of bending of the client's neck.

Figure 5B:
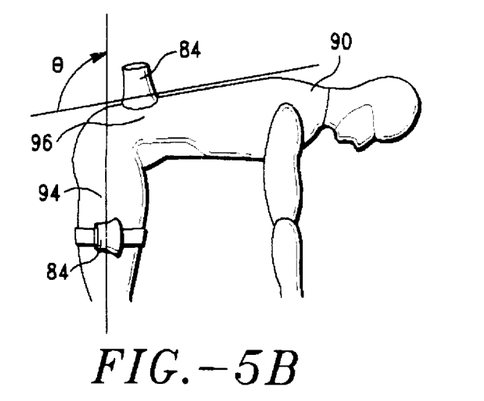

FIG. 5b shows a pair of inclinometers 48 cooperating to gauge lumbar and hip flexion. One attaches to the leg 94 of the client 90. The other attaches to the lumbar spine 96.

Figure 5C:
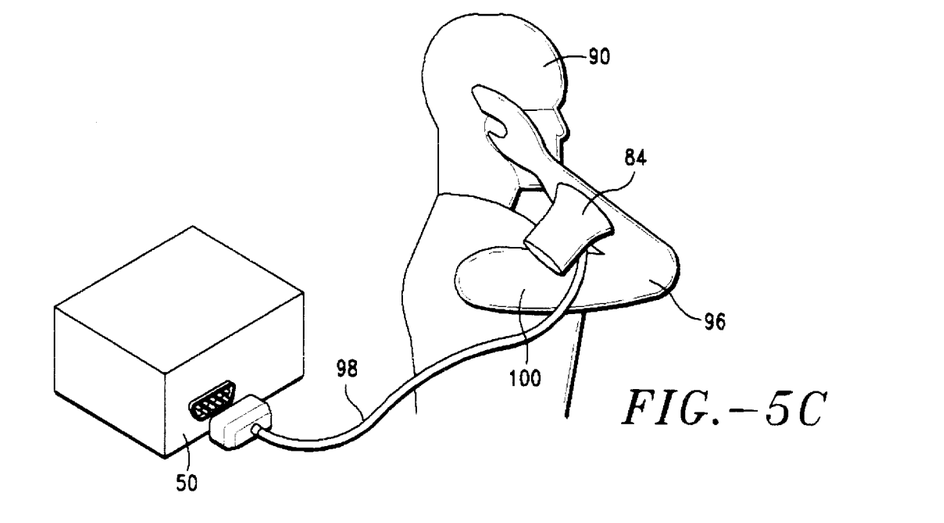

FIG. 5c shows the rear of the first terminal computer 50 and an inclinometer 48. The inclinometer 84 connects to the parallel port of the computer 50 via a standard parallel port cable 98.

The inclinometer measures flexion of the elbow 96. It can be appreciated that when the upper arm 100 is horizontal with respect to the floor, desktop or other reference surface, that only a single inclinometer 84 need by used to measure elbow 98 flexion.

Figure 5D:
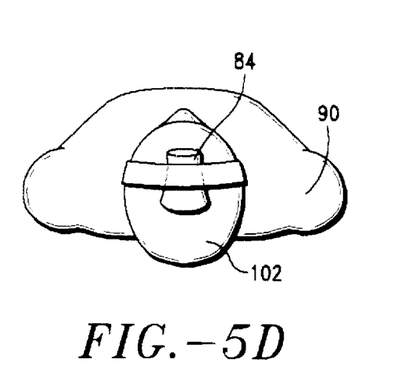

FIG. 5d shows an inclinometer 84 attached to the top of the head 102 of a client 90. Accordingly, measurements relating to neck rotation can be taken, stored, and compared to gauge client progress where a client 90 undergoes therapy to improve neck rotation.

Figure 5E:
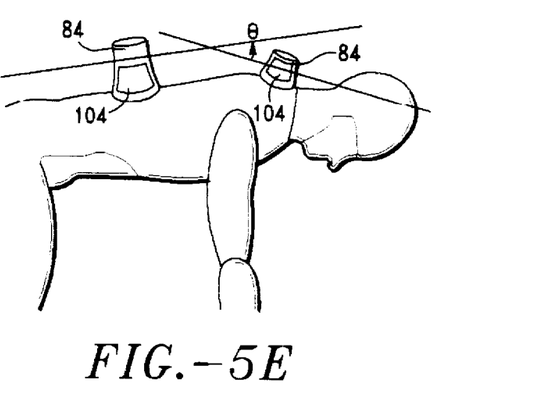

FIG. 5e shows an inclinometer 84 having a visually readable gauge 104 for displaying postural information. Because the gauge 104 is visually readable, a therapist using the system of the present invention can visually inspect the inclinometer 84 from a remote location.

While the foregoing detailed description has described various embodiments of the invention it is to be understood that the above description is illustrative only and not limiting of the disclosed invention. Any of a number of postural and bodily function measurement devices may be used to communicate client postural information and feedback over the communication link. Accordingly, the invention is to be limited only by the appended claims.

What is claimed is:

1. A method for remotely providing physical therapy services to a human client having a physical condition, comprising:
    (a) providing a first terminal associated with a client, a second terminal associated with a therapist, and video communication link between the terminals;
    (b) instructing the client, via the communication link, to move in a particular manner, or to assume a sustained posture;
    (c) measuring client postural information with a postural measurement device coupled to the first terminal;
    (d) communicating feedback, including video signals and client postural information data, via the communication link, from the first terminal to the second terminal relating to the movement or sustained posture;
    (e) utilizing the feedback to assess the physical condition of the client; and
    (f) communicating remedial movements or a remedial sustained posture to the client to address the physical condition.

2. A method as set forth in claim 1, wherein steps b, and c, repeat to iteratively address the physical condition.

3. A method as set forth in claim 1, wherein steps b, c, d, and e repeat to iteratively address the physical condition.

4. A method as set forth in claim 1, further comprising: simultaneously communicating the client postural information, video data and audio data from the first terminal to the second terminal via the communication link.

5. A method as set forth in claim 1, wherein the communication link includes a satellite communication link providing sufficient bandwidth to simultaneously communicate audio, video and other data between the client and the therapist.

6. A method as set forth in claim 1, further comprising: providing a medical history data base; and
    communicating client medical history from the database to the second terminal to provide the therapist with a client medical history.

7. A method as set forth in claim 1, wherein the step of providing a communication link includes linking the first terminal and second terminals with the Internet.

8. A system for remotely providing physical therapy services to a client having a physical condition, comprising:
(a) a first terminal associated with the client having a video camera, microphone, speaker and display;
(b) a second terminal associated with a therapist having a video camera, microphone, speaker and display;
(c) a postural measurement device coupled with the first terminal for measuring client postural information; and
(d) a video communication link between the first terminal and the second terminal to communicate audio, video and postural information between the first terminal and the second terminal.

9. A system as set forth in claim 8, wherein the postural measurement device includes an inclinometer is positioned in visual communication with the first terminal camera, the inclinometer displays client postural information, the camera views the displayed postural information and communicates a video image of the inclinometer and the postural information to the second terminal.

10. A system as set forth in claim 8, wherein the postural measurement device includes an infrared transmitter;
the first terminal includes an infrared receiver; and
the postural measurement device communicates client postural information to the first terminal receiver with the infrared transmitter, the first terminal communicates the postural information to the second terminal via the communication link.

11. A system as set forth in claim 10, wherein the postural measurement device includes an inclinometer.

12. A system as set forth in claim 10, wherein the postural measurement device includes an accelerometer.

13. A system as set forth in claim 10, wherein the postural measurement device includes a goiniometer.

14. A system as set forth in claim 10, wherein the postural measurement device includes a dynamometer.

15. A system as set forth in claim 10, wherein the postural measurement device includes a sphygnomanometer.

16. A system as set forth in claim 10, wherein the postural measurement device includes a skin surface EMG measurement device to detect changes in skin surface EMG for any of a variety of postures.

17. A system as set forth in claim 10, wherein the postural measurement device includes a thermometer to measure changes in body temperature at a selected location, for any of a variety of postures.

18. A system as set forth in claim 10, wherein the postural measurement device includes a protractor positioned in visual communication with respect to the camera of the first terminal.

19. A system as set forth in claim 10, wherein the first terminal camera is remotely controllable by the second terminal.

20. A system as set forth in claim 10, wherein the first terminal camera includes a stereoscopic 3-D video camera and the first terminal display displays stereoscopic images.

21. A system as set forth in claim 10, wherein the second terminal includes a computer for processing video images to extract client postural information from the video images.

* * * * *